United States Patent [19]

DeCamp et al.

[11] Patent Number: 4,864,035

[45] Date of Patent: Sep. 5, 1989

[54] HYDROGENATION PROCESS FOR THE FORMATION OF TETRAHYDRO HMG-COA REDUCTASE INHIBITORS

[75] Inventors: Ann E. DeCamp, N. Plainfield; Thomas R. Verhoeven, Cranford; Ichiro Shinkai, Westfield, all of N.J.

[73] Assignee: Merck & Co., Inc., Rahway, N.J.

[21] Appl. No.: 92,801

[22] Filed: Sep. 3, 1987

[51] Int. Cl.[4] ..................... C07F 7/18; C07D 309/30
[52] U.S. Cl. ..................... 549/214; 549/292
[58] Field of Search ............... 549/214, 292

[56] References Cited

U.S. PATENT DOCUMENTS

| | | | |
|---|---|---|---|
| 4,351,844 | 9/1982 | Patchett et al. | 424/279 |
| 4,444,784 | 4/1984 | Hoffman et al. | 549/292 |
| 4,584,389 | 4/1986 | Sletzinger et al. | 549/292 |

OTHER PUBLICATIONS

Evans et al., "Rhodium(I)-Catalyzed, etc", JACS 106 3866 (1984).
Crabtree et al., I, "Occurrence and Origin, etc", Organometallics, 2, 682 (1983).
Schruck et al., "Catalytic Hydrogenation, etc", CA 85:123066p (1976).
Crabtree et al., I, "Cationic Iridium, etc", CA 88:31361q (1978).
Santos et al., "Catalytic Activity and, etc", CA 100:180758t (1984).

Primary Examiner—Richard L. Raymond
Attorney, Agent, or Firm—Melvin Winokur; Joseph F. DiPrima

[57] ABSTRACT

A novel hydrogenation process, using a homogenous iridium or rhodium catalyst for the reduction of both double bonds of des-(α-methylbutyryl)-C-8-hydroxy lovastatin and C-8-amino, C-8-alkoxy and C-6-substituted analogs, is disclosed.

20 Claims, No Drawings

HYDROGENATION PROCESS FOR THE FORMATION OF TETRAHYDRO HMG-COA REDUCTASE INHIBITORS

BACKGROUND OF THE INVENTION

The trans-fused tetrahydro derivative (I) of lovastatin was found by Patchett et al. (U.S. Pat. No. 4,351,844) to be a potent HMG-CoA reductase inhibitor, and as such is an effective antihypercholesterolemic agent. The cis-fused adduct appears to have no antihypercholesterolemic activity. Patchett et al. disclose a catalytic hydrogenation procedure for preparing (I)

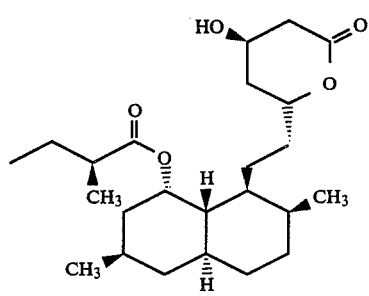

I from lovastatin. Thiss process involves hydrogenation over platinum oxide in ethyl acetate. However, the product formed, at best, is a mixture of 60% trans and 40% cis-tetrahydrolovastatin. The desired trans isomer could be isolated from this mixture only after silica gel chromatographic purification.

Sletzinger et al. (U.S. Pat. No. 4,584,389) improved on the trans/cis ratio in the reduction product mixture by using platinum on alumina as the hydrogenation catalyst. Using this catalyst the yield of trans-fused product was increased to 65–75%, however, this process also produced a partially reduced dihydro by-product which although present in small amounts (1–5%) was quite difficult to remove by either chromatography or crystallization.

DETAILED DESCRIPTION OF THE INVENTION

The novel process of this invention may be depicted as:

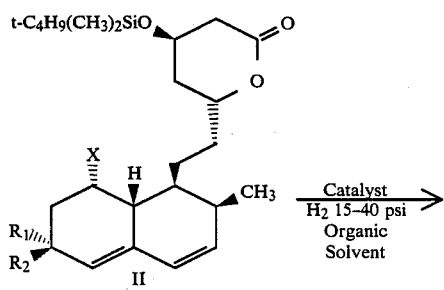

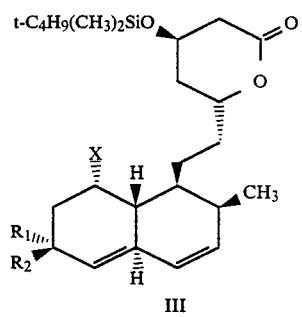

III wherein

X is OH, or $NH_2$ or OR; wherein R is $C_{1-5}$ alkyl, $C_{3-7}$ cycloalkyl, phenyl-$C_{1-3}$ alkyl, substituted phenyl-$C_{1-3}$ alkyl in which the substituent is halogen, $CF_3$ or CN;

$R_1$ is H or $CH_3$ or $CH_2OSi(Me)_2t$-$C_4H_9$ or $OSi(Me)_2$-t—$C_4H_9$;

$R_2$ is H or $CH_2OSi(Me)_2t$-$C_4H_9$ or $OSi(Me)_2t$-$C_4H_9$; provided that when $R_1$ or $R_2$ is $CH_2OSi(Me)_2t$-$C_4H_9$ the other is H; and one and only one of $R_1$ and $R_2$ can be $OSi(Me)_2t$-$C_4H_9$.

Alternatively:

$R_1$ is H or $CH_3$ or $CH_2OSi(Me)_2t$-$C_4H_9$;

$R_2$ is H or $CH_2OSi(Me)_2t$-$C_4H_9$; provided that when $R_1$ or $R_2$ is $CH_2OSi(Me)_2t$-$C_4H_9$ the other is H.

Catalyst is $[Ir(COD)PCy_3(pyr)]PF_6$ or $[Rh(NBD)(DIPHOS-4)]BF_4$;

Organic Solvent is dichloromethane, chloroform, chlorobenzene or a like substance.

Tert-butyldimethylsilyl is shown as a hydroxyl protecting group. It will be clear to those skilled in the art that other hydroxyl protecting groups such as tert-butyldiphenylsilyl, trimethylsilyl, triethylsilyl, triisopropylsilyl and tetrahydropyranyl could be substituted for tert-butyldimethylsilyl without effecting the outcome of the instant invention.

The instant process reduces both double bonds of des-(α-methylbutyryl)-C-8-hydroxy-lovastatin and C-8-amino, C-8-alkoxy and C-6-substituted analogs. The present invention provides for formation of the trans-fused tetrahydro product (III) in essentially 100% yield and uncontaminated (<1%) with any dihydro derivatives.

The products (III) where X is OH can be acylated at C-8 to yield a variety of C-8-acyloxy derivatives. The acylation can be conducted following the procedure of Hoffman, et al. U.S. Pat. No. 4,444,784 or that described in copending U.S. application Ser. No. 038580 filed Apr. 15, 1987. The hydroxyl compounds can also be converted into C-8-amido derivatives following the procedure exemplified in U.S. Pat. No. 4,472,726, and C-8-alkoxy derivatives following essentially the procedure in U.S. Pat. No. 4,282,155.

Products (III) where X is $NH_2$ can be converted into C-8-amido derivatives following the procedure exemplified in U.S. Pat. No. 4,472,426.

One embodiment of the present invention is the preparation of compounds of structure (III) wherein X is OH. This embodiment is exemplified by compounds wherein:

a. $R_1=CH_3$, $R_2=H$;
b. $R_1=CH_2OSi(Me)_2t$-$C_4H_9$, $R_2=H$;
c. $R_1=H$, $R_2=CH_2OSi(Me)_2t$-$C_4H_9$.
d. $R_1=OSi(Me)_2t$-$C_4H_9$, $R_2=H$;

e. R₁=H, R₂=OSi(Me)₂t-C₄H₉;
f. R₁=CH₃, R₂=OSi(Me)₂t-C₄H₉.

A second embodiment of the present invention is the preparation of compounds of structure (III) wherein X is NH₂. This embodiment is exemplified by compounds wherein:

a. R₁=CH₃, R₂=H;
b. R₁=CH₂OSi(Me)₂t-C₄H₉, R₂=H;
c. R₁=H, R₂=CH₂OSi(Me)₂t-C₄H₉;
d. R₁=OSi(Me)₂t-C₄H₉; R₂=H;
e. R₁=H, R₂=OSi(Me)₂t-C₄H₉;
f. R₁=CH₃, R₂=OSi(Me)₂t-C₄H₉.

A third embodiment of the present invention is the preparation of compounds of structure (III) wherein X is OR. In one class of this embodiment R is OCH₃ or p-fluorobenzyl. This embodiment is exemplified by compounds wherein:

a. R=OCH₃, R₁=CH₃, R₂=H;
b. R=p-fluorobenzyl, R₁=CH₃, R₂=H;
c. R=OCH₃, R₁=CH₂OSi(Me)₂t-C₄H₉, R₂=H
d. R=p-fluorobenzyl, R₁=CH₃, R₂=H
e. R=OCH₃, R₁=H, R₂=CH₂OSi(Me)₂t-C₄H₉
f. R=p-fluorobenzyl, R₁=H, R₂=CH₂OSi(Me)₂t-C₄H₉.
g. R=OCH₃, R₁=OSi(Me)₂t-C₄H₉, R₂=H;
h. R=OCH₃, R₁=H, R₂=OSi(Me)₂t-C₄H₉;
i. R=OCH₃, R₁=CH₃, R₂=OSi(Me)₂t-C₄H₉;
j. R=p-fluorobenzyl, R₁=OSi(Me)₂t-C₄H₉, and R₂=H;
k. R=p-fluorobenzyl, R₁=H, R₂=OSi(Me)₂t-C₄H₉;
l. R=p-fluorobenzyl, R₁=CH₃, R₂=OSi(Me)₂t-C₄H₉.

The rhodium catalyst may be [Ir(COD)PCy₃(pyr)]PF₆ (COD=1,5-cyclooctadiene, PCy₃=tricyclohexylphosphine, pyr=pyridine) or [Rh(NBD)(DIPHOS-4)]BF₄ (NBD=Norbornadiene, DIPHOS-4=1,4-bis(diphenylphosphino)butane), preferably [Ir(COD)PCy₃(pyr)]PF₆. The iridium catalyst can be prepared following the procedure of Crabtree et al., *J. Organomet. Chem* 135, 395 (1977). The rhodium catalyst may be prepared following the procedure of Stille et al., *J. Org. Chem.*, 47, 468 (1982) as supplemented by Evans et al., *J. Am. Chem. Soc.*, 106, 3866 (1984). The organic solvent is dichloromethane or chloroform or chlorobenzene or a like substance, preferably dichloromethane.

The starting diene wherein X=OH, R₁=CH₃ and R₂=H may be prepared following the hydrolysis procedure of Hoffman et al., U.S. Pat. No. 4,444,784. Dienes wherein X=OH, R₁=CH₂OSi(Me)₂t-C₄H₉ or R₂=CH₂OSi(Me)₂t-C₄H₉ are prepared following the procedure outlined in copending U.S. patent application Ser. No. 048136 filed May 15, 1987, followed by protection of the 6-hydroxymethyl with t-C₄H₉(Me)₂-SiCl and hydrolysis of the C-8 acyl moiety as described above. Starting dienes wherein X=OR can be prepared from the hydroxyl analog following the procedure described in U.S. Pat. No. 4,282,155. Starting dienes wherein X=NH₂ can be prepared from the hydroxyl analog following the procedure in U.S. Pat. No. 4,472,426.

The olefinic substrate and catalyst in approximately 0.5-10.0 mole percent catalyst to substrate, preferably 2.5 mole percent are dissolved in an organic solvent at a temperature of 25°–80° C., preferably 25° C. under a pressure of 15–40 psi, preferably 40 psi for about 24 hours. The solution is worked up following standard procedures and the solvent evaporated to yield a crystalline product.

The following Examples illustrate the present invention and as such are not to be considered as limiting the invention set forth in the claims appended hereto.

EXAMPLE 1

Preparation of
6(R)-[2-[8(S)-hydroxy-2(S),6(S)-dimethyl-1,2,3,4,4a(R),5,6,7,8,8a(S)-decahydronaphthyl-1(S)]ethyl]-4(R-tert butyl-dimethylsilyloxy-3,4,5,6-tetrahydro-2H-pyran-2-one A solution of 6(R)-[2-[8(S)-hydroxy-2(S),6(R)-dimethyl-1,2,3,4,4a(R),5,6,7,8,8a(R)-hexahydronaphthyl-1(S)]ethyl]-4(R-tert butyl-dimethylsilyloxy-3,4,5,6-tetrahydro-2H-pyran-2-one (1.365 g, 3.13 mmol) in dichloromethane (15 ml) was purged briefly with argon gas. [Ir(COD)(PCy₃)(pyr)]PF₆ (62.5 mg, 2.5 mole percent) was added and the solution reduced at ambient temperature under 40 psi of hydrogen pressure for 24 hours. The solution was evaporated in vacuo to a solid which was taken up in 50 ml of warm diethyl ether, filtered through a one inch bed of Florisil® (Magnesium silicate filter aid used to retain any catalyst complex which remained in solution), washed with 45 ml of warm diethyl ether and evaporated in vacuo to give the title compound as a pale cream-colored solid. ¹H NMR (300 MHz, CDCl₃), δ 4.66 (m, 1H), 4.28 (m, 1H), 4.08 (m, 1H), 2.47-2.68 (m, 2H), 0.92-2.14 (m), 0.87 (s, 9H), 0.82 (d, J=2 Hz, 3H), 0.07 (s, 3H), 0.05 (s, 3H).

EXAMPLES 2–24

Following the procedure substantially as described in Example 1 but substituting for the diene used as starting material therein, approximately equal molar amounts of the compounds of structure (II) as described below there are prepared the tetrahydro analogs (III).

|  | X | R₁ | R₂ |
|---|---|---|---|
| Example 2 | OH | CH₂OSi(Me)₂t-C₄H₉ | H |
| Example 3 | OH | H | CH₂OSi(Me)₂t-O₄H₉ |
| Example 4 | NH₂ | CH₃ | H |
| Example 5 | NH₂ | CH₂OSi(Me)₂t-C₄H₉ | H |
| Example 6 | NH₂ | H | CH₂OSi(Me)₂t-C₄H₉ |
| Example 7 | OCH₃ | CH₃ | H |
| Example 8 | OCH₃ | CH₂OSi(Me)₂t-C₄H₉ | H |
| Example 9 | OCH₃ | H | CH₂OSi(Me)₂t-C₄H₉ |
| Example 10 | 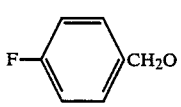 | CH₃ | H |

| | X | R₁ | R₂ |
|---|---|---|---|
| Example 11 | F-C₆H₄-CH₂O | CH₂OSi(Me)₂t-C₄H₉ | H |
| Example 12 | F-C₆H₄-CH₂O | H | CH₂OSi(Me)₂t-C₄H₉ |
| Example 13 | OH | OSi(Me)₂t-C₄H₉ | H |
| Example 14 | OH | H | OSi(Me)₂t-C₄H₉ |
| Example 15 | OH | CH₃ | OSi(Me)₂t-C₄H₉ |
| Example 16 | NH₂ | OSi(Me)₂t-C₄H₉ | H |
| Example 17 | NH₂ | H | OSi(Me)₂t-C₄H₉ |
| Example 18 | NH₂ | CH₃ | OSi(Me)₂t-C₄H₉ |
| Example 19 | OCH₃ | OSi(Me)₂t-C₄H₉ | H |
| Example 20 | OCH₃ | H | OSi(Me)₂t-C₄H₉ |
| Example 21 | OCH₃ | CH₃ | OSi(Me)₂t-C₄H₉ |
| Example 22 | F-C₆H₄-CH₂O | OSi(Me)₂t-C₄H₉ | H |
| Example 23 | F-C₆H₄-CH₂O | H | OSi(Me)₂t-C₄H₉ |
| Example 24 | F-C₆H₄-CH₂O | CH₃ | OSi(Me)₂t-C₄H₉ |

What is claimed is:

1. A process for the preparation of a compound of structural formula (III):

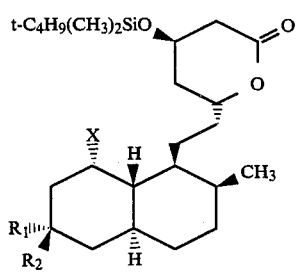

wherein:
X is OH, NH₂, or OR; wherein R is $C_{1-5}$ alkyl, $C_{3-7}$ cycloalkyl, phenyl $C_{1-3}$ alkyl, substituted phenyl $C_{1-3}$ alkyl in which the substituent is halogen, CF₃ or CN;
R₁ is H or CH₃ or CH₂OSi(Me)₂t-C₄H₉ or OSi(Me)₂t-C₄H₉;
R₂ is H or CH₂OSi(Me)₂t-C₄H₉ or OSi(Me)₂t-C₄H₉; provided that when R₁ or R₂ is CH₂OSi(Me)₂t-C₄H₉ the other is H; and one and only one of R₁ and R₂ can be OSi(Me)₂t-C₄H₉;
which comprises:
contacting a compound of structural formula (II)

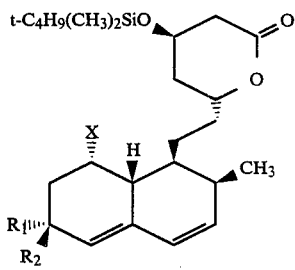

with 1,5-cyclooctadiene(tricyclohexylphosphine)(pyridinium)iridium(I) hexafluorophosphate or norbornadiene-1,4-bis(diphenylphosphino)butane rhodium (I) tetrafluoroborate in an organic solvent at a temperature of about 25°–80° C. under a hydrogen gas pressure of about 15–40 psi.

2. A process of claim 1 wherein the catalyst is 1,5-cyclooctadiene(tricyclohexylphosphine)(pyridine)iridium(I) hexafluorophosphate.

3. A process of claim 2 wherein the organic solvent is dichloromethane or chloroform or chlorobenzene.

4. A process of claim 3 wherein the organic solvent is dichloromethane.

5. A process of claim 4 wherein the temperature is about 25° C.

6. A process of claim 5 wherein the hydrogen gas pressure is about 40 psi.

7. A process of claim 1 wherein
R₁ is H or CH₃ or CH₂OSi(Me)₂t-C₄H₉;

$R_2$ is H or $CH_2OSi(Me)_2t$-$C_4H_9$; provided that when $R_1$ or $R_2$ is $CH_2OSi(Me)_2t$-$C_4H_9$ the other is H.

8. A process of claim 1 wherein X is OH.

9. A process of claim 8 wherein the compound (III) prepared is selected from the group wherein:
 a. $R_1=CH_3$, $R_2=H$;
 b. $R_1=CH_2OSi(Me)_2t$-$C_4H_9$, $R_2=H$;
 c. $R_1=H$, $R_2=CH_2OSi(Me)_2t$-$C_4H_9$;
 d. $R_1=OSi(Me)_2t$-$C_4H_9$; $R_2=H$;
 e. $R_1=H$, $R_2=OSi(Me)_2t$-$C_4H_9$;
 f. $R_1=CH_3$, $R_2=OSi(Me)_2t$-$C_4H_9$.

10. A process of claim 1 wherein X is $NH_2$.

11. A process of claim 10 wherein the compound (III) is selected from the group wherein:
 a. $R_1=CH_3$, $R_2=H$;
 b. $R_1=CH_2OSi(Me)_2t$-$C_4H_9$, $R_2=H$;
 c. $R_1=H$, $R_2=CH_2OSi(Me)_2t$-$C_4H_9$;
 d. $R_1=OSi(Me)_2t$-$C_4H_9$; $R_2=H$;
 e. $R_1=H$, $R_2=OSi(Me)_2t$-$C_4H_9$;
 f. $R_1=CH_3$, $R_2=OSi(Me)_2t$-$C_4H_9$.

12. A process of claim 1 wherein X is OR.

13. A process of claim 12 wherein X is $OCH_3$.

14. A process of claim 13 wherein the compound (III) prepared is selected from the group wherein:
 a. $R_1=CH_3$, $R_2=H$;
 b. $R_1=CH_2OSi(Me)_2t$-$C_4H_9$, $R_2=H$;
 c. $R_1=H$, $R_2=CH_2OSi(Me)_2t$-$C_4H_9$;
 d. $R_1=OSi(Me)_2t$-$C_4H_9$; $R_2=H$;
 e. $R_1=H$, $R_2=OSi(Me)_2t$-$C_4H_9$;
 f. $R_1=CH_3$, $R_2=OSi(Me)_2t$-$C_4H_9$.

15. A process of claim 12 wherein X is p-fluorobenzyloxy.

16. A process of claim 15 wherein the compound (III) prepared is selected from the group wherein:
 a. $R_1=CH_3$, $R_2=H$;
 b. $R_1=CH_2OSi(Me)_2t$-$C_4H_9$, $R_2=H$;
 c. $R_1=H$, $R_2=CH_2OSi(Me)_2t$-$C_4H_9$;
 d. $R_1=OSi(Me)_2t$-$C_4H_9$; $R_2=H$;
 e. $R_1=H$, $R_2=OSi(Me)_2t$-$C_4H_9$;
 f. $R_1=CH_3$, $R_2=OSi(Me)_2t$-$C_4H_9$.

17. A process of claim 9 wherein the catalyst is 1,5-cyclooctadiene(tricyclohexylphosphine)(pyridine)iridium(I) hexafluorophosphate, the solvent is dichloromethane, the hydrogen gas pressure is about 40 psi, and the temperature is about 25° C.

18. A process of claim 11 wherein the catalyst is 1,5-cyclooctadiene(tricyclohexylphosphine)(pyridine)iridium(I) hexafluorophosphate, the solvent is dichloromethane, the hydrogen gas pressure is about 40 psi, and the temperature is about 25° C.

19. A process of claim 14 wherein the catalyst is 1,5-cyclooctadiene(tricyclohexylphosphine)(pyridine)iridium(I) hexafluorophosphate, the solvent is dichloromethane, the hydrogen gas pressure is about 40 psi, and the temperature is about 25° C.

20. A process of claim 16 wherein the catalyst is 1,5-cyclooctadiene(tricyclohexylphosphine)(pyridine)iridium(I) hexafluorophosphate, the solvent is dichloromethane, the hydrogen gas pressure is about 40 psi, and the temperature is about 25° C.

* * * * *